United States Patent
Eriksen et al.

(10) Patent No.: US 9,757,439 B2
(45) Date of Patent: Sep. 12, 2017

(54) PEPTIDE VACCINE COMPRISING MUTANT RAS PEPTIDE AND CHEMOTHERAPEUTIC AGENT

(71) Applicant: Targovax ASA, Oslo (NO)

(72) Inventors: Jon Amund Eriksen, Oslo (NO); Gustav Gaudernack, Oslo (NO)

(73) Assignee: TARGOVAX ASA, Oslo (NO)

( * ) Notice: Subject to any disclaimer, the term of this patent is extended or adjusted under 35 U.S.C. 154(b) by 0 days.

(21) Appl. No.: 15/308,917

(22) PCT Filed: May 5, 2015

(86) PCT No.: PCT/EP2015/059861
§ 371 (c)(1),
(2) Date: Nov. 4, 2016

(87) PCT Pub. No.: WO2015/169804
PCT Pub. Date: Nov. 12, 2015

(65) Prior Publication Data
US 2017/0065694 A1    Mar. 9, 2017

(30) Foreign Application Priority Data

May 6, 2014    (EP) .................................... 14167265

(51) Int. Cl.
| A61K 39/00 | (2006.01) |
| A61K 31/7068 | (2006.01) |
| C07K 14/82 | (2006.01) |
| A61K 45/06 | (2006.01) |
| A61K 35/17 | (2015.01) |

(52) U.S. Cl.
CPC ...... *A61K 39/0011* (2013.01); *A61K 31/7068* (2013.01); *A61K 35/17* (2013.01); *A61K 45/06* (2013.01); *C07K 14/82* (2013.01); *A61K 2039/5158* (2013.01); *A61K 2039/545* (2013.01); *A61K 2039/55522* (2013.01); *A61K 2039/585* (2013.01)

(58) Field of Classification Search
None
See application file for complete search history.

(56) References Cited

FOREIGN PATENT DOCUMENTS

| GB | 2328689 A | 3/1999 |
| WO | 92/14756 A1 | 9/1992 |
| WO | 00/66153 A1 | 11/2000 |
| WO | 2014/0110408 A1 | 7/2014 |
| WO | 2015/086590 A2 | 6/2015 |

OTHER PUBLICATIONS

Pubmed Ras protein Search—Jan. 6, 2017.*
Abrams, S.I. et al., "Mutant ras epitopes as targets for cancer vaccines," MPSRCH GENBANK, Abstract (Feb. 1996). Two pages.
Altschul, S.F. et al., "Gapped BLAST and PSI-BLAST: a new generation of protein database search programs," Nucleic Acids Research, 25(17):3389-3402 (1997). Fourteen pages.
Bauer, C. et al., "Concomitant gemcitabine therapy negatively affects DC vaccine-induced CD8+ T-cell and B-cell responses but improves clinical efficacy in a murine pancreatic carcinoma model," Cancer Immunol Immunother, 53:321-333 (2014). Thirteen pages.
Boon, T., "Toward a Genetic Analysis of Tumor Rejection Antigens," Adv. Can Res., 58:177-211 (1992). Eighteen pages.
Conroy, T. et al., "FOLFIRINOX versus Gemcitabine for Metastatic Pancreatic Cancer," New England Journal of Medicine, 364(19):1817-1825 (2011). Ten pages.
Dermer, G.B., "Another Anniversary for the War on Cancer," Biotechnology, 12(3):320 (1994). Four pages.
Ezzell, C., "Cancer 'Vaccines': An Idea Whose Time Has Come?" J. NIH Res. 7:46-49 (1995). Four pages.
Freshney, R.I., "Culture of Animal Cells, A Manual of Basic Technique," Alan R. Liss, Inc., (1983). Four pages.
Gedde-Dahl, III, T. et al. "T-cell Responses Against Products of Oncogenes: Generation and Characterization of Human T-Cell Clones Specific for p21 Ras-Derived Synthetic Peptides," Human Immunology, 33:266-274 (1992). Nine pages.
Gjertsen, M.K. et al., "Intradermal RAS Peptide Vaccination With Granulocyte-Macrophage Colony-Stimulating Factor as Adjuvant: Clinical and Immunological Responses in Patients With Pancreatic Adenocarcinoma," International Journal of Cancer, 92:441-450 (2001). Ten pages.
Gjertsen, M.K. et al., "Vaccination with mutant ras peptides and induction of T-cell responsiveness in pancreatic carcinoma patients carrying the corresponding RAS mutation," MPSRCH GENBANK, Abstract (Nov. 25, 1995). Two pages.
Golan, T. et al., "A phase I trial of a local delivery siRNA against k-ras in combination with chemotherapy for locally advanced pancreatic adenocarcinoma," Journal of Clinical Oncology, Abstract, 31(15) (May 20, 2013). One page.
Gura, T., "Systems for Identifying New Drugs Are Often Faulty," Science, 278:1041-1042 (Nov. 1997). Two pages.
Haigh, P.I. et al., "Vaccine Therapy for Patients With Melanoma," Oncology, 13:1561-1582 (Nov. 1999). Fifteen pages.
Hunger, R.E. et al., "Successful induction of immune responses against mutant ras in melanoma patients using intradermal injection of peptides and GM-CSF as adjuvant," Exp. Dermatology, 10:161-167 (2001). Seven pages.
Jain, R.K., "Barriers to Drug Delivery in Solid Tumors," Sci. Am., 271(1):58-65 (Jul. 1994). Eight pages.
Johansen, B.H. et al., "Binding of Ras Oncogene Peptides to Purified HLA-DQ(α1*0102, β1*0602) and -DR(α, 31*0101) Molecules," Scandinavian Journal of Immunology, 39:607-612 (1994). Seven pages.
Johnson, R.K. et al., "The clinical impact of screening and other experimental tumor studies," Cancer Treatment Reviews, 2:1-31 (1975). Thirty-one pages.

(Continued)

Primary Examiner — Elly-Gerald Stoica
(74) Attorney, Agent, or Firm — HoustinHogle LLP

(57) ABSTRACT

There is disclosed at least one peptide suitable for eliciting an immune response, for use in the treatment of cancer. The, or each, peptide corresponds to a fragment of the RAS protein, but has one to three point mutations thereof. The at least one peptide is for use in the treatment of cancer by simultaneous or sequential administration with an antimetabolite chemotherapeutic agent.

18 Claims, 1 Drawing Sheet

(56) References Cited

OTHER PUBLICATIONS

Khleif, S.N. et al., "A phase I vaccine trial with peptides reflecting ras oncogene mutations of solid tumors," MPSRCH GENBANK, Abstract (Mar. 1999). Two pages.
Lurquin, C. and Boon, T. et al., "Structure of the Gene of Tum-Transplantation Antigen P91A: The Mutated Exon Encodes a Peptide Recognized with Ld by Cytolytic T Cells," Cell, 58:293-303 (Jul. 28, 1989). Eleven pages.
Oettle, H. et al., "Adjuvant Chemotherapy With Gemcitabine vs Observation in Patients Undergoing Curative-Intent Resection of Pancreatic Cancer," JAMA, 297(3):267-277 (Jan. 17, 2007). Eleven pages.
Pion, S. et al., "Shaping the Repertoire of Cytotoxic T-Lymphocyte Responses: Explanation for the Immunodominance Effect Whereby Cytotoxic T Lymphocytes Specific for Immunodominant Antigens Prevent Recognition of Nondominant Antigens," Blood, 93(3):952-962 (Feb. 1999). Twelve pages.
Prior, I.A. et al., "A comprehensive survey of Ras mutations in cancer," Cancer Research, 72(10):2457-2467 (May 15, 2012). Twenty pages.
Réjiba, S. et al., "K-ras oncogene silencing strategy reduces tumor growth and enhances gemcitabine chemotherapy efficacy for pancreatic cancer treatment," Cancer Science, 98(7):1128-1136 (Jul. 2007). Nine pages.
Spitler, L.E., "Cancer Vaccines: The Interferon Analogy," Cancer Biotherapy, 10(1):1-3 (1995). Three pages.
Strimpakos, A.S. et al., "Update on Phase I Studies in Advanced Pancreatic Adenocarcinoma. Hunting in Darkness?" Highlights from the "2013 ASCO Annual Meeting." Chicago, IL (May 30-Jun. 4, 2013); Journal of the Pancreas, 14(4):354-358 (Jul. 10, 2013). Five pages.
UniProtKB/Swiss-Prot accession No. P01112.1. Nineteen pages.
Wedén, S. et al., "Long-term follow-up of patients with resected pancreatic cancer following vaccination against mutant K-ras," International Journal of Cancer, 128(5):1120-1128 (May 12, 2010). Nine pages.
Wijermans, P.W. et al., "Severe immunodeficiency in patients treated with fludarabine monophosphate," European Journal of Haematology, 50(5):292-296 (May 1993). Five pages.
Xue, W. et al., "Small RNA combination therapy for lung cancer," Proceedings of the National Academy of Sciences of the United States of America, 111(34):E3553-E3561 (Aug. 2014). Nine pages.
International Search Report and Written Opinion of the International Searching Authority, mailed on Jun. 18, 2015, from International Application No. PCT/EP2014/077033, filed on Dec. 9, 2014. Twenty-two pages.
International Preliminary Report on Patentability of the International Preliminary Examining Authority, mailed on Feb. 8, 2016, from International Application No. PCT/EP2014/077033, filed on Dec. 9, 2014. Nine pages.
Applicant Response, dated Jan. 11, 2016, to Written Opinion of the International Preliminary Examining Authority for International Application No. PCT/EP2014/077033, filed on Dec. 9, 2014. Eight pages.
International Search Report and Written Opinion of the International Searching Authority, mailed on Nov. 6, 2015, from International Application No. PCT/EP2015/059861, filed on May 5, 2015. Fifteen pages.
International Preliminary Report on Patentability of the International Preliminary Examining Authority, mailed on Sep. 21, 2016, from International Application No. PCT/EP2015/059861, filed on May 5, 2015. Ten pages.
PCT Demand for International Preliminary Examination (Chapter II), filed on Mar. 7, 2016, from International Application No. PCT/EP2015/059861, filed on May 5, 2015. Nine pages.
PCT Response to Written Opinion of the International Preliminary Examining Authority, filed on Jun. 1, 2016, from International Application No. PCT/EP2015/059861, filed on May 5, 2015. Eleven pages.
PCT Response to Invitation, filed on Jun. 29, 2016, from International Application No. PCT/EP2015/059861, filed on May 5, 2015. Ten pages.
Coulie, P.G. et al., "Tumour antigens recognized by T lymphocytes: At the core of cancer immunotherapy," Nature Reviews Cancer, 14:135-146 (Feb. 2014). Thirteen pages.
Guo, C. et al., "Therapeutic Cancer Vaccines: Past, Present and Future," Adv Cancer Res. Author manuscript, Pub in final edited form: 119:421-475 (2013). Forty-five pages.
Pardoll, D.M., "The blockade of immune checkpoints in cancer immunotherapy," Nature, 12:252-264 (Apr. 2012). Thirteen pages.
Black, C.A., "Delayed Type Hypersensitivity: Current Theories with an Historic Perspective," Dermatology Online Journal, 5(1):7 (1999). Ten pages.
Neoptolemos, J.P. et al., "Adjuvant Chemotherapy With Fluorouracil Plus Folinic Acid vs Gemcitabine Following Pancreatic Cancer Resection: A Randomized Controlled Trial," JAMA, 304(10):1073-1081 (Sep. 8, 2010). Nine pages.
Nestle, F.O. et al., "Vaccination of melanoma patients with peptide- or tumor lysate-pulsed dendritic cells," Nature Medicine, 4(3):328-332 (Mar. 1998). Five pages.
Oettle, H. et al., "Adjuvant Chemotherapy With Gemcitabine and Long-term Outcomes Among Patients With Resected Pancreatic Cancer," JAMA, 310(14):1473-1481 (Oct. 9, 2013). Nine pages.
Sinn, M. et al., Perioperative treatment options in resectable pancreatic cancer—how to imporove long-term survival, World J. Gastrointenst Oncol, 8(3):248-257 (Mar. 15, 2016). Eleven pages.
Uesaka, K. et al., Adjuvant chemotherapy of S-1 versus gemcitabine for resected pancreatic cancer: a phase 3, open-label, randomised, non-inferiority trial (JASPCA 01), The Lancet, 388:248-257 (Jul. 16, 2016). Ten pages.
Van Laethem, J.L. et al., "Adjuvant Gemcitabine Alone Versus Gemcitabine-Based Chemoradiotherapy After Curative Resection for Pancreatic Cancer: A Randomized EORTC-40013-22012/FFCD-9203/GERCOR Phase II Study," J Clinical Oncol, 28(29):4450-4456 (Oct. 10, 2010). Seven pages.

* cited by examiner

PEPTIDE VACCINE COMPRISING MUTANT RAS PEPTIDE AND CHEMOTHERAPEUTIC AGENT

RELATED APPLICATIONS

This application is a §371 National Phase Application of international Application No. PCT/EP2015/059861, filed on May 5, 2015, which claims priority to European Application No. 14167265.9, filed on May 6, 2014, both of which are incorporated herein by reference in their entirety.

INCORPORATION BY REFERENCE OF MATERIAL IN ASCII TEXT FILE

This application incorporates by reference the Sequence Listing contained in the following ASCII text file:
File name: 0348-0002US1_PN814035LTS_Sequence_Listing.TXT; created Oct. 13, 2016, 8 KB in size.

FIELD OF THE INVENTION

The present invention provides at least one peptide of the RAS protein for use in the treatment of cancer. The invention also relates to a pharmaceutical preparation of the at least one peptide for such use.

BACKGROUND OF THE INVENTION

The genetic background for the onset of cancer is alterations in proto-oncogenes, oncogenes and tumour suppressor genes. Proto-oncogenes are normal genes of the cell which have the potential of becoming oncogenes. All oncogenes code for and function through a protein. In the majority of cases they have been shown to be components of signal transduction pathways. Oncogenes arise in nature from proto-oncogenes through point mutations or translocations, thereby resulting in a transformed state of the cell harbouring the mutation. Cancer develops through a multi-step process involving several mutational events in oncogenes and tumour suppressor cells In its simplest form, a single base substitution in a proto-oncogene may cause the encoded protein to differ in one amino acid.

In experimental models involving murine tumours, it has been shown that point mutations in intracellular "self"-proteins may give rise to tumour rejection antigens consisting of peptides differing in a single amino acid from the normal peptide. The T cells recognizing these peptides in the context of major histocompatibility (MHC) molecules on the surface of the tumour cells are capable of killing the tumour cells and thus rejecting the tumour from the host. (Boon, T. et al, Cell 1989, Vol. 58, p. 293-303)

In the last three decades, particular effort has been devoted to the analysis of antibodies to human tumour antigens. It has been suggested that such antibodies could be used both for diagnostic and therapeutic purposes, for instance in connection with an anti-cancer agent. One problem is that antibodies can only bind to tumour antigens that are exposed on the surface of tumour cells. For this reason the efforts to produce a cancer treatment based on the immune system of the body has been less successful than expected.

Antibodies typically recognise free antigens in native conformation and can potentially recognise almost any site exposed on the antigen surface. In contrast to the antibodies produced by B cells, T cells recognise antigens only in the context of MHC molecules, designated HLA (human leukocyte antigen) in humans, and only after appropriate antigen processing, usually consisting of proteolytic fragmentation of the protein, resulting in peptides that fit into the groove of the MHC molecules. This enables T cells to recognise peptides derived from intracellular proteins. T cells can thus recognise aberrant peptides derived from anywhere in the tumour cell, when displayed on the surface of the tumour cell by MHC molecules. The T cell can subsequently be activated to eliminate the tumour cell harbouring the aberrant peptide.

T cells may control the development and growth of cancer by a variety of mechanisms. Cytotoxic T cells, both HLA class I restricted CD8+ and HLA Class II restricted CD4+, may directly kill tumour cells carrying the appropriate tumour antigens. CD4+ helper T cells are needed for induction and maintenance of cytotoxic T cell responses as well as for antibody responses, and for inducing macrophage and lymphokine-activated killer cell (LAK cell) killing.

Many oncogenes and their protein products have been identified. In addition, it has been shown that the T cell repertoire of a healthy person includes T cells with specificity against a synthetic peptide fragment derived from one p21 RAS oncogene product, when presented on an appropriate HLA molecule. Furthermore, it is anticipated that approximately 20% of all cancers are associated with a mutation in the RAS oncogene.

WO 92/14756 discloses synthetic peptides and fragments of oncogene protein products which elicit T cell immunity, for use in vaccines against cancers associated with RAS and compositions for the treatment of cancer. The peptides correspond to an active fragment of the oncogene as presented by the cancer cell and include a mutation in one or more positions corresponding to the oncogene mutation. This document discloses mutations at positions 12, 13 and 61 of the RAS protein and specifically discloses G12A, G12V, G12C, G12S, G12K, G12D, G12R, Q61R, Q61K, Q61L, Q61H, G13V and G13D mutations. While this document mentions that vaccines may comprise a selection of peptides having the most common mutations found in oncogene proteins, it does not suggest any specific combinations of peptides.

WO 00/66153 discusses synthetic peptide mixtures which elicit T cell immunity for use in cancer vaccines. The peptide mixtures consist of RAS p21 mutant peptides and this document specifically discloses G12A, G12C, G12D, G12R, G12S, G12V, Q61H, Q61K, Q61L, Q61R and G13D mutations. This document also discloses that the immune response elicited by a cocktail of peptides was significantly higher than that elicited by a single peptide. However, it does not suggest the use of a peptide vaccine in a combined treatment of cancer with any other form of therapy.

Gjertsen et al. (Int. J. Cancer 2001, 92, p. 441-450) discloses a phase I/II trial involving patients with adenocarcinoma of the pancreas vaccinated with synthetic mutant RAS peptides in combination with granulocyte-macrophage colony-stimulating factor. This trial used single peptide vaccines or a mixture of four mutant peptides. The combination vaccine consisted of the four most common K-RAS mutations found in pancreatic adenocarcinoma, namely peptides having a G12V, a G12D, a G12C or a G12R mutation. This document does not suggest that combination therapy with anti-metabolite chemotherapeutic agents may be effective.

Wedén et al. (Int. J. Cancer 2010, 128(5), p. 1120-1128) reports the long-term follow-up of patients with pancreatic adenocarcinoma vaccinated with synthetic mutant RAS peptides. The vaccine consisted of either a single RAS peptide or a cocktail of seven RAS peptides. In particular, the seven RAS peptides used in this trial had a G12A, a G12C, a G12D, a G12R, a G12S, a G12V or a G13D mutation. There is no mention of a combination therapy with anti-metabolite chemotherapeutic agents.

Prior et al. (Cancer Res. 2012, 72(10), p. 2457-2467) discloses that different types of cancer are coupled to mutation of a particular RAS isoform and that each isoform has a distinctive codon mutation signature. In addition, Prior et al. discloses that a total of 18 mutations occur in positions 12, 13 and 61 of the RAS protein, with six mutations occurring in each position. This review also discusses the effects of these mutations on RAS function and the potential mechanisms leading to differential patterns of RAS isoform mutations.

A previously unrelated treatment of cancer patients has been systemic administration of the chemotherapeutic agent gemcitabine. Gemcitabine is currently a frequent chemotherapeutic treatment for patients with various cancers, such as non-small cell lung cancer, pancreatic cancer, bladder cancer and breast cancer. In particular, gemcitabine is frequently used to treat advanced pancreatic cancer.

Gemcitabine is an anti-metabolite chemotherapeutic agent, specifically a pyrimidine analogue. The triphosphate analogue of gemcitabine replaces cytidine during DNA replication and incorporation into the elongating DNA strand halts further DNA synthesis after addition of one more nucleotide as the DNA polymerase is unable to proceed. Further mechanisms of action are thought to include inhibition of ribonucleoside reductase, leading to a depletion of deoxyribonucleotide pools necessary for DNA synthesis, and competition with deoxycytidine triphosphate as an inhibitor of DNA polymerase. These actions result in necrosis, leading to an arrest of tumour growth. This action also means that anti-metabolite chemotherapeutic agents are toxic to other actively dividing cells such as T cells. The preferred regimen involves using chemotherapy first, followed by vaccination to enhance later induction of immune responses from killed cancer cells.

While some drug combinations, such as FOLFIRINOX, have been shown to be more effective than gemcitabine in patients with metastatic pancreatic adenocarcinoma, therapy with this combination was associated with a high incidence of side effects (Conroy et al., N Engl J Med 2011, vol. 364(19), P. 1817-1825). It is desirable, therefore, to find novel strategies for the treatment of cancer.

Oettle et al. (JAMA 2007, 297(3), p. 267-277) reports an investigation of the use of gemcitabine as adjuvant chemotherapy in resectable pancreatic cancer, and discloses that the effect of gemcitabine on disease-free survival was significant in patients with either R0 or R1 resection. In particular, this study discloses that postoperative gemcitabine significantly delayed the development of recurrent disease after complete resection of pancreatic cancer, compared to patients to whom gemcitabine was not administered following resection. However, this study does not suggest that gemcitabine could be useful in combination with other pharmaceutical treatments of cancer.

Bauer et al. (Cancer Immunol. Immunother. 2014, 63, p. 321-333), discloses that gemcitabine has a negative influence on dendritic cell (DC) vaccine-induced T-cell proliferation. In particular, this study showed that delayed administration of gemcitabine, as compared to the DC vaccine, did not improve patient's immune response, while concomitant administration of gemcitabine and the DC vaccine significantly impaired the vaccine-induced immune response.

Thus, there is a need to provide further and more effective cancer treatments.

SUMMARY OF INVENTION

The present invention arises because it has now surprisingly been found that the administration of a RAS peptide vaccine in combination with an anti-metabolite chemotherapeutic agent (gemcitabine) significantly improved the immune response of patients as compared to the administration of the RAS peptide vaccine alone. This was unexpected because it had previously been believed that administering an anti-metabolite chemotherapeutic agent, such as gemcitabine, to a patient causes cell death of proliferating immune cells, including proliferating T cells, which would thereby reduce the activity of the patient's immune system and thus lower the immune response of the patient to a peptide vaccine that is administered simultaneously or sequentially. While not wishing to be bound by theory, it is believed that, in fact, the cell death caused by the anti-metabolite chemotherapeutic agent may result in the release of signalling molecules which creates a systemic immunogenic environment, thereby promoting already induced immune responses and promoting further induced immune responses. Thus the immune response to the peptide vaccine is actually enhanced, rather than reduced, by the anti-metabolite chemotherapeutic agent.

In a first aspect of the invention, there is provided at least one peptide, suitable for eliciting an immune response, wherein the or each peptide corresponds to a fragment of the RAS protein but has one to three point mutations thereof, for use in the treatment of cancer by simultaneous or sequential administration with an anti-metabolite chemotherapeutic agent.

Advantageously, the or each peptide comprises a region of at least 8 amino acids which includes position 12 or 13 of the RAS protein, wherein said region has at least 6 amino acid residues, other than at position 12 or 13 respectively, which are identical to the corresponding region of the RAS protein, and wherein the or each peptide has a point mutation at the amino acid residue corresponding to said position 12 or 13 respectively.

Conveniently, one of said point mutations is selected from a G13A, G13C, G13D, G13R, G13S, G13V, G12A, G12C, G12D, G12R, G12S or a G12V mutation.

Preferably, the at least one peptide comprises two or more peptides, each peptide having a different point mutation.

Advantageously, the at least one peptide comprises:
a peptide having a G13D mutation
a peptide having a G12A mutation
a peptide having a G12C mutation
a peptide having a G12D mutation
a peptide having a G12R mutation
a peptide having a G12S mutation, and
a peptide having a G12V mutation,
preferably wherein the at least one peptide comprises a peptide consisting of the sequence represented by SEQ ID NO: 13, a peptide consisting of the sequence represented by SEQ ID NO: 14, a peptide consisting of the sequence represented by SEQ ID NO: 15, a peptide consisting of the sequence represented by SEQ ID NO: 16, a peptide consisting of the sequence represented by SEQ ID NO: 17, a peptide consisting of the sequence represented by SEQ ID NO: 18 and a peptide consisting of the sequence represented by SEQ ID NO: 19.

Conveniently, the at least one peptide comprises:
a peptide having a G13D mutation
a peptide having a G13C mutation
a peptide having a G12A mutation
a peptide having a G12C mutation
a peptide having a G12D mutation
a peptide having a G12R mutation
a peptide having a G12S mutation, and
a peptide having a G12V mutation,
preferably wherein the at least one peptide comprises a peptide consisting of the sequence represented by SEQ ID NO: 13, a peptide consisting of the sequence represented by SEQ ID NO: 14, a peptide consisting of the sequence represented by SEQ ID NO: 15, a peptide consisting of the sequence represented by SEQ ID NO: 16, a peptide consisting of the sequence represented by SEQ ID NO: 17, a peptide consisting of the sequence represented by SEQ ID NO: 18, a peptide consisting of the sequence represented by SEQ ID NO: 19 and a peptide consisting of the sequence represented by SEQ ID NO: 20.

Preferably, the anti-metabolite chemotherapeutic agent is a pyrimidine analogue, or pharmaceutically acceptable salt thereof.

Advantageously, the pyrimidine analogue is gemcitabine, or a pharmaceutically acceptable salt thereof.

Conveniently, the cancer comprises cells which express a mutated RAS protein.

Preferably, the cancer is pancreatic cancer.

Conveniently, the pancreatic cancer is resected pancreatic cancer.

Advantageously, the anti-metabolite chemotherapeutic agent is first administered at least three weeks after the first dose of the at least one peptide.

Conveniently, the anti-metabolite chemotherapeutic agent is first administered 12 weeks or fewer after surgical resection of pancreatic cancer.

Preferably, the anti-metabolite chemotherapeutic agent is administered within 24 hours of the at least one peptide.

Advantageously, the anti-metabolite chemotherapeutic agent is administered after the at least one peptide has been administered.

Conveniently, the at least one peptide is administered at a dosage of 0.01-10 mg, preferably 0.1-2 mg, and more preferably 0.7 mg per dose.

Preferably, the anti-metabolite chemotherapeutic agent is administered at a dosage of 100-10,000 mg/m², preferably 500-2000 mg/m², and more preferably 1000 mg/m².

Advantageously, the at least one peptide and the anti-metabolite chemotherapeutic agent are administered simultaneously or sequentially at at least two instances, and more preferably at at least three instances, wherein each instance of administration is separated by at least one week, and more preferably by at least 2 weeks.

In a second aspect of the invention, there is provided at least one T-cell specific for the at least one peptide according to the first aspect described above, or a T-cell preparation comprising T-cells specific for the at least one peptide according to the first aspect described above when presented on an MHC molecule, for use in the treatment of cancer by simultaneous or sequential administration with an anti-metabolite chemotherapeutic agent.

In a third aspect of the invention, there is provided a pharmaceutical composition comprising at least one peptide according to the first aspect above, or at least one T-cell or a T-cell preparation according to the second aspect above, for use in the treatment of cancer by combined or sequential administration with an anti-metabolite chemotherapeutic agent.

In a fourth aspect of the invention, there is provided a kit comprising a first product comprising at least one peptide, T cell or pharmaceutical composition according to the first, second or third aspect described above, respectively, and a second product comprising a supply of an anti-metabolite chemotherapeutic agent as described in the aspects above.

In a fifth aspect of the invention, there is provided a method of treatment of cancer comprising administering to a patient in need thereof at least one peptide, T cell or pharmaceutical composition, as described in the first, second or third aspect above, respectively, and an anti-metabolite chemotherapeutic agent as described in the aspects above.

The term "peptide" as used herein, refers to a polymer of amino acid residues that is (or has a sequence that corresponds to) a fragment of a longer protein. The term also applies to amino acid polymers in which one or more amino acid residues is a modified residue, or a non-naturally occurring residue, such as an artificial chemical mimetic of a corresponding naturally-occurring amino acid, as well as to naturally occurring amino acid polymers.

The percentage "identity" between two sequences may be determined using the BLASTP algorithm version 2.2.2 (Altschul, Stephen F., Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", Nucleic Acids Res. 25:3389-3402) using default parameters. In particular, the BLAST algorithm can be accessed on the internet using the URL http://www.ncbi.nlm.nih.gov/blast/.

The term "immune response", as used herein, refers in some embodiments to a T cell-mediated immune response upon presentation of a peptide by major histocompatibility (MHC) molecules on the surface of cells, and in particular refers to activation of T cells upon presentation of peptide.

The term "RAS protein", as used herein, refers to the class of small GTPase proteins encoded by the ras proto-oncogene and includes all three isoforms of the RAS protein: HRAS, KRAS and NRAS. In some embodiments, the term "RAS protein" refers to the protein corresponding to UniProtKB/Swiss-Prot accession number P01112.1 and as shown in SEQ ID NO:23.

The term "position 13 of the RAS protein", as used herein, refers to the thirteenth amino acid in the amino acid chain forming the primary structure of the wild-type RAS protein, counting from the N-terminal.

The term "position 12 of the RAS protein", as used herein, refers to the twelfth amino acid in the amino acid chain forming the primary structure of the wild-type RAS protein, counting from the N-terminal.

The term "the amino acid corresponding to position 13", as used herein, means an amino acid in a peptide of a RAS protein located in the peptide's amino acid chain at a position corresponding to the thirteenth amino acid of the amino acid sequence of the RAS protein, counting from the N-terminal. A corresponding meaning is attributed to the term "the amino acid corresponding to position 12".

The term "RAS protein mutations", as used herein, refers to one or more point mutations present in the RAS proteins present in a sample taken from a subject.

The term "point mutation", as used herein, refers to the replacement of a single amino acid residue in the polypeptide chain of a protein product with a different amino acid residue.

The term "one to three point mutations", as used herein, means one point mutation or two point mutations or three point mutations.

The term, for example, "a G12V mutation", as used herein, refers to a point mutation which has resulted in the glycine (G) at position 12 of the wild-type RAS protein being replaced with valine (V). Similar definitions apply to similar terms, such as G13C, G13R, etc.

The term "pharmaceutical composition", as used herein, means a pharmaceutical preparation suitable for administration to an intended human or animal subject for therapeutic purposes.

The term "anti-metabolite chemotherapeutic agent", as used herein, means a product having the effect of inhibiting a patient's cell growth or cell division and used as a therapeutic treatment of cancer.

The term "gemcitabine", as used herein, means the compound having the IUPAC name 4-amino-1-(2-deoxy-2,2-difluoro-β-D-erythro-pentofuranosyl)pyrimidin-2(1H)-on, which has the following structural formula:

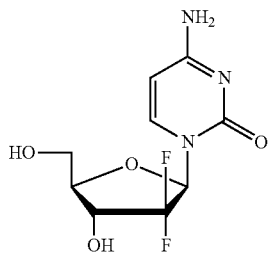 [SMILES: Nc1ccn([C@@H]2O[C@H](CO)[C@H](O)C2(F)F)c(=O)n1]

The term "a pharmaceutically acceptable salt thereof", as used herein, means a salt formed by allowing the free form compound to react with an acid or base. Examples of pharmaceutically acceptable salts include hydrohalogenic acid salts such as hydrofluorides, hydrochlorides, hydrobromides, and hydroiodides; inorganic acid salts such as hydrochlorides, nitrates, perchlorates, sulfates and phosphates; lower alkanesulfonic acid salts such as methanesulfonates, trifluoromethanesulfonates, and ethanesulfonates; arylsulfonic acid salts such as benzenesulfonates, and p-toluenesulfonates; organic acid salts such as acetates, malates, fumarates, succinates, citrates, ascorbates, tartrates, oxalates, and maleates; alkali metal salts such as sodium salts, potassium salts, and lithium salts; alkaline earth metal salts such as calcium salts and magnesium salts; metal salts such as aluminum salts and iron salts; inorganic salts such as ammonium salts; amine salts including organic salts such as t-octylamine salts, dibenzylamine salts, morpholine salts, glucosamine salts, phenylglycine alkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzylphenethylamine salts, piperazine salts, tetramethylammonium salts, and tris(hydroxymethyl)aminomethane salts; and amino acid salts such as glycine salts, lysine salts, arginine salts, ornithine salts, glutamates, and aspartates.

The term "sequential administration", as used herein, means administration of two products to a patient wherein the two products are not administered simultaneously. In some embodiments each instance of sequential administration means that the two products are each administered less than 5 days, 4 days, 3 days, 2 days or 1 day apart.

BRIEF DESCRIPTION OF THE SEQUENCE LISTINGS

Figures 1, 2:
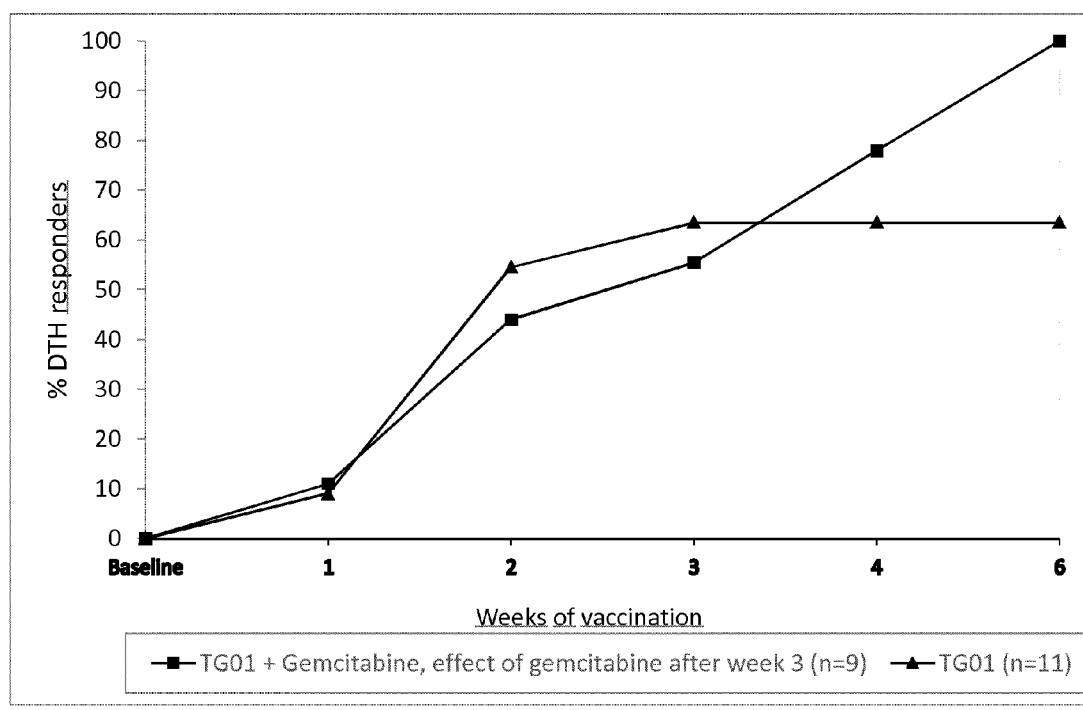
FIG. 1 is a table showing the time point at which a positive DTH response was recorded in each patient. [1]DTH not assessed; [2]NT: No treatment.
FIG. 2 is a graph showing the synergistic adjuvant effect after onset of gemcitabine on DTH responses, during induction of an immune response.

SEQ ID NO:1 shows an amino acid sequence of the RAS peptide having a G13C mutation.
SEQ ID NO:2 shows an amino acid sequence of the RAS peptide having a G13R mutation.
SEQ ID NO:3 shows an amino acid sequence of the RAS peptide having a G13D mutation.
SEQ ID NO:4 shows an amino acid sequence of the RAS peptide having a G13V mutation.
SEQ ID NO:5 shows an amino acid sequence of the RAS peptide having a G13A mutation.
SEQ ID NO:6 shows an amino acid sequence of the RAS peptide having a G13S mutation.
SEQ ID NO:7 shows an amino acid sequence of the RAS peptide having a G12A mutation.
SEQ ID NO:8 shows an amino acid sequence of the RAS peptide having a G12C mutation.
SEQ ID NO:9 shows an amino acid sequence of the RAS peptide having a G12D mutation.
SEQ ID NO:10 shows an amino acid sequence of the RAS peptide having a G12R mutation.
SEQ ID NO:11 shows an amino acid sequence of the RAS peptide having a G12S mutation.
SEQ ID NO:12 shows an amino acid sequence of the RAS peptide having a G12V mutation.
SEQ ID NO: 13 shows an amino acid sequence of the RAS peptide of TG01 and TG02 having a G13D mutation.
SEQ ID NO: 14 shows an amino acid sequence of the RAS peptide of TG01 and TG02 having a G12A mutation.
SEQ ID NO: 15 shows an amino acid sequence of the RAS peptide of TG01 and TG02 having a G12C mutation.
SEQ ID NO: 16 shows an amino acid sequence of the RAS peptide of TG01 and TG02 having a G12D mutation.
SEQ ID NO: 17 shows an amino acid sequence of the RAS peptide of TG01 and TG02 having a G12R mutation.
SEQ ID NO: 18 shows an amino acid sequence of the RAS peptide of TG01 and TG02 having a G12S mutation.
SEQ ID NO: 19 shows an amino acid sequence of the RAS peptide of TG01 and TG02 having a G12V mutation.
SEQ ID NO: 20 shows an amino acid sequence of the RAS peptide of TG02 having a G13C mutation.
SEQ ID NO: 21 shows an alternative amino acid sequence of the RAS peptide having a G13R mutation.
SEQ ID NO: 22 shows an alternative amino acid sequence of the RAS peptide having a G13V mutation.
SEQ ID NO: 23 shows the full length amino acid sequence of the wild-type RAS protein.

DETAILED DESCRIPTION OF THE INVENTION

The invention relates, in general terms, to at least one peptide of the RAS protein for use in the treatment of cancer by simultaneous or sequential administration with an antimetabolite chemotherapeutic agent. Each peptide of the at least one peptide has one to three point mutations of the RAS protein.

The or each peptide for use according to the invention may be a peptide corresponding to any of HRAS, KRAS or NRAS. All three of these RAS isoforms share sequence identity in all of the regions responsible for GDP/GTP binding, i.e. the regions subject to mutation in cancer.

In preferred embodiments, at least one of said one to three point mutations is a point mutation that corresponds to a mutation encoded by a RAS oncogene, for example at positions 12, 13 or 61 of the RAS protein.

In some embodiments, the or each peptide comprises at least 8, at least 9, at least 10, at least 12, at least 16, at least 17, at least 18, at least 20, at least 24 or at least 30 amino acids. In preferred embodiments, the or each of the at least one peptide comprises at least 8 amino acids. In other preferred embodiments, the or each of the at least one peptide comprises at least 17 amino acids.

In some embodiments, the or each peptide comprises a region of at least 8 amino acid residues which includes position 12 or 13 of the RAS protein. In preferred embodiments, the point mutation of the or each peptide is at the amino acid residue at said position 12 or 13.

In some embodiments, the or each peptide has at least 20%, at least 25%, at least 30%, at least 37%, at least 50%, at least 60%, at least 66%, at least 75%, at least 85%, at least 95%, at least 99% or 100% sequence identity at positions other than the region including position 13 with the RAS protein. In some embodiments, the or each peptide has at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs 1-6. In preferred embodiments, the or each peptide has at least 95% sequence identity at positions other than the region including position 13 to one of SEQ ID NOs: 1-6. In other embodiments, the or each peptide has 100% sequence identity at positions other than the region including position 13 to one of SEQ ID NOs: 1-6.

In some embodiments, the at least one peptide comprises a first peptide having a percentage sequence identity at positions other than the region including position 13 to one of SEQ ID NOs: 1-6 and a second peptide has a different percentage sequence identity at positions other than the region including position 13 to a different one of SEQ ID NOs: 1-6. In other embodiments, a first peptide has a percentage sequence identity at positions other than the region including position 13 to one of SEQ ID NOs: 1-6 and a second peptide has the same percentage sequence identity at positions other than the region including position 13 to a different one of SEQ ID NOs: 1-6. In all embodiments the or each peptide is capable of eliciting an immune response.

Each of the first and second peptides of the at least one peptide of the embodiment above has a point mutation at position 13 of the RAS protein, wherein the point mutation in the first peptide is different from the point mutation in the second peptide. The wild-type RAS protein comprises glycine (G) at position 13. Thus, the mutation at position 13 may be a point mutation from glycine to any other amino acid. However, G13A, G13C, G13D, G13R, G13S and G13V mutations have been found to be particularly associated with cancer. Thus, in preferred embodiments, the point mutation of the or each peptide is independently one of a G13A, G13C, G13D, G13R, G13S or a G13V mutation. In more preferred embodiments, the point mutation at position 13 of one of the first and second peptides is independently a G13C or a G13D mutation. In particularly preferred embodiments, the point mutation at position 13 of one of the first or second peptides is a G13C mutation. In other particularly preferred embodiments, the point mutation at position 13 of one of the first or second peptides is a G13D mutation.

In some embodiments, the point mutation at position 13 of the first or second peptide is a G13C mutation and the point mutation at position 13 of the other peptide is a G13D mutation.

In other embodiments, the point mutation at position 13 of the first or second peptide is a G13R mutation and the point mutation at position 13 of the other peptide is a G13V mutation.

In some embodiments, there are two or more peptides of the RAS protein, having one to three point mutations thereof, for use in a method of treatment of cancer by simultaneous or sequential administration with an antimetabolite chemotherapeutic agent. Each of the second or more peptides independently comprises at least 8, at least 9, at least 10, at least 12, at least 16, at least 17, at least 18, at least 20, at least 24 or at least 30 amino acids. In preferred embodiments, each of the peptides comprises at least 8 amino acids. In other preferred embodiments, each of the peptides comprises at least 17 amino acids. In further embodiments, each of the peptides comprises at least 18 amino acids. In general, each peptide in the peptide mixture may comprise a different number of amino acids to one or more of the other peptides. Each of the peptides has at least one point mutation which is different from the point mutation of the other peptide(s).

In alternative embodiments of the invention, the at least one peptide may comprise at least a third peptide of the RAS protein comprising a region of at least 8 amino acids including position 13 of the RAS protein. The at least third peptide may have a point mutation at the amino acid corresponding to position 13 of the RAS protein that is different to the position 13 mutations of the first and second peptides. The point mutation may be one of a G13A, G13C, G13D, G13R, G13S or a G13V mutation, independently of the point mutations of the first and second peptides.

The at least one peptide of the invention may additionally comprise at least one further peptide of the RAS protein comprising a region of at least 8 amino acids. In some embodiments, said region of the at least one further peptide includes position 12 of the RAS protein.

In embodiments where the at least one peptide comprises at least a third peptide, each of the peptides independently comprises at least 8, at least 9, at least 10, at least 12, at least 16, at least 17, at least 18, at least 20, at least 24 or at least 30 amino acids. In preferred embodiments, each of the peptides comprises at least 8 amino acids. In other preferred embodiments, each of the peptides comprises at least 17 amino acids. In further embodiments, each of the peptides comprises at least 18 amino acids. In general, each peptide of the at least one peptide may comprise a different number of amino acids to one or more of the other peptides of the at least peptide.

In embodiments where the at least one peptide comprises at least one peptide comprising a region including position 12 of the RAS protein, the amino acid corresponding to position 12 of the RAS protein has a point mutation. In the wild-type RAS protein, the amino acid of position 12 is glycine (G). Thus, in some embodiments, the point mutation at position 12 may be to an amino acid other than glycine. In some embodiments, each mutation is, independently, a G12A, G12C, G12D, G12R, G12S or a G12V mutation. In other embodiments, the at least one further peptide has at least 20%, at least 25%, at least 30%, at least 40%, at least 50%, at least 60%, at least 66%, at least 75%, at least 85%, at least 95%, at least 99% or 100% sequence identity at positions other than the region including position 12 with the RAS protein. In some embodiments, the at least one peptide has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NO: 7-12. In some embodiments, there is more than one peptide of the RAS protein comprising a region of at least 8 amino acids including position 12 of the RAS protein and having a point mutation at the amino acid corresponding to position 12 of the RAS protein. In such embodiments, each of the peptides having a position 12 mutation has a different point mutation.

In some embodiments, the at least one peptide comprises at least two peptides of the RAS protein, each comprising a region of at least 8 amino acids including position 12 of the RAS protein. The point mutation at position 12 may be one of a G12A, G12C, G12D, G12R, G12S or a G12V mutation. The at least two peptides including position 12 of the RAS protein may have at least 20%, at least 25%, at least 30%, at least 40%, at least 50%, at least 60%, at least 66%, at least 75%, at least 85%, at least 95%, at least 99% or 100% sequence identity at positions other than the region including position 12 with the RAS protein. In some embodiments, the at least two peptides comprising a region of at least 8 amino acids including position 12 has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NOs: 7-12 and 14-19. Any combination of the above-mentioned mutations and SEQ ID NOs is envisaged in the at least one peptide for use according to the present invention.

In some embodiments, the at least one peptide consists of a peptide having a G13D mutation, a peptide having a G12A mutation, a peptide having a G12C mutation, a peptide having a G12D mutation, a peptide having a G12R mutation, a peptide having a G12S mutation, and a peptide having a G12V mutation. In such embodiments, the at least one peptide peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 3, 7, 8, 9, 10, 11 and 12. In some embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 13-19. This embodiment of the invention is herein referred to as TG01 when there is 100% sequence identity to SEQ ID NOs: 13-19. Table 3 shows the peptides which are preferably present in TG01.

In some embodiments, the at least one peptide consists of a peptide having a G13C mutation, a peptide having a G13D mutation, a peptide having a G12A mutation, a peptide having a G12C mutation, a peptide having a G12D mutation, a peptide having a G12R mutation, a peptide having a G12S mutation, and a peptide having a G12V mutation. In such embodiments, the at least one peptide peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 1, 3, 7, 8, 9, 10, 11 and 12. In some embodiments, the peptide mixture consists of peptides independently having at least 20%, at least 25%, at least 30%, at least 40%, at least 50%, at least 60%, at least 66%, at least 75%, at least 85%, at least 95%, at least 99% or 100% sequence identity at positions other than the region including positions 12 or 13 respectively to SEQ ID NOs: 13-20. This embodiment of the invention is herein referred to as TG02 when there is 100% sequence identity to SEQ ID NOs: 13-20. Table 4 shows the peptides which are preferably present in TG02.

In general, the or each of the at least one peptide for use according to the present invention, within a region of 8 amino acids including position 12 or 13, has at least 6 amino acid residues, other than the residue at position 12 or 13 respectively, which are identical to the corresponding region of the RAS protein. Furthermore, in general, the or each of the at least one peptide for use according to the present invention, at positions other than the region including position 12 or 13 of the RAS protein has at least 20%, at least 25%, at least 30%, at least 40%, at least 50%, at least 60%, at least 66%, at least 75%, at least 85%, at least 95%, at least 99% or 100% to one of SEQ ID NOs: 1-20, respectively.

In some embodiments, the at least one peptide consists of a first, second, third and fourth peptide. The first and second peptides each has a point mutation at position 13 of the RAS protein, wherein the point mutation in the first peptide is different from the point mutation in the second peptide. The point mutation of each of the first and second peptides is independently one of a G13A, G13C, G13D, G13R, G13S or a G13V mutation. Each of the third and fourth peptides comprises a region of at least 8 amino acids including position 13 of the RAS protein, and each of the third and fourth peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 13 with the RAS protein. Each of the third and fourth peptides may independently have at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs: 1-6, 20, 13, 21 or 22. Each of the third and fourth peptides has a point mutation at the amino acid corresponding to position 13 of the RAS peptide, and each of the first, second, third and fourth peptides has a point mutation that is different from the point mutations of the other peptides. In one embodiment, the first peptide is a peptide having a G13R mutation, the second peptide is a peptide having a G13A mutation, the third peptide is a peptide having a G13S mutation and the fourth peptide is a peptide having a G13V mutation.

In some embodiments, the at least one peptide consists of a maximum of 8 different peptides. In other embodiments, there is a maximum of 10, 12, 14 or 16 different peptides. In embodiments comprising more than one peptide, the at least one peptide may comprise 1, 2, 3, 4, 5 or 6 peptides comprising a region of at least 8 amino acid residues including position 12 of the RAS protein. In other embodiments comprising more than one peptide, the at least one peptide may comprise 1, 2, 3, 4, 5 or 6 peptides comprising a region of at least 8 amino acids residues including position 13 of the RAS protein. In further embodiments, the at least one peptide comprises 1, 2, 3, 4, 5 or 6 peptides independently comprising a region of at least 8 amino acid residues including position 12 or 13 of the RAS protein.

In some embodiments, the or each peptide comprising a region of at least 8 amino acids including position 13 of the RAS peptide comprises positions 1 to 30 of the RAS protein. In alternative embodiments, the or each peptide comprising a region of at least 8 amino acids including position 13 of the RAS protein comprises positions 5 to 21 of the RAS protein. In further embodiments, the amino acid corresponding to position 13 of the RAS protein is at the C-terminus of the each peptide. In further embodiments, the amino acid corresponding to position 13 of the RAS protein is at the N-terminus of the or each peptide. In general, the region having at least 8 amino acids including position 13 of the RAS protein may consist of any 8 positions of the RAS protein including position 13. For example, the region having at least 8 amino acids including position 13 may consist of the amino acids from position 6 to position 13, position 7 to position 14, position 8 to position 15, position 9 to position 16, position 10 to position 17, position 11 to position 18, position 12 to position 19 or position 13 to position 20 of the RAS protein.

In some embodiments, the peptides comprising a region of at least 8 amino acids including position 12 of the RAS peptide comprise positions 1 to 30 of the RAS protein. In other embodiments, the peptides comprising a region of at least 8 amino acids including position 12 of the RAS protein comprises positions 5 to 21 of the RAS protein. In alternative embodiments, the amino acid corresponding to position 12 of the RAS protein is at the C-terminus of the peptide. In further embodiments, the amino acid corresponding to position 12 of the RAS protein is at the N-terminus of the peptide. In general, the region having at least 8 amino acids including position 12 of the RAS protein may consist of any 8 positions of the RAS protein including position 12. For example, the region having at least 8 amino acids including position 12 may consist of the amino acids from position 5 to position 12, position 6 to position 13, position 7 to position 14, position 8 to position 15, position 9 to position 16, position 10 to position 17, position 11 to position 18 or position 12 to position 19 of the RAS protein.

In embodiments comprising more than one peptide, the more than one peptide may comprise different peptides in equal or in different proportions. For example, in embodiments consisting of a first and a second peptide, the first and second peptides are used in equal proportions, i.e. each peptide comprises 50% of the peptides used. In other embodiments, there is a greater proportion of the first peptide than the second peptide. For example, the first peptide may comprise at least 55%, at least 60%, at least 70%, at least 80% or at least 90% of the peptides used. In alternative embodiments, a greater proportion of the second peptide is used than the first peptide. For example, the second peptide may comprise at least 55%, at least 60%, at least 70%, at least 80% or at least 90% of the peptides used. In embodiments wherein more than two peptides are used, the peptides may be used in equal or in different proportions from each other. For example, each of the peptides may independently comprise at least 1%, at least 5%, at least 10%, at least 20% at least 30%, at least 40%, at least 50%, at least 60%, at least 60%, at least 70%, at least 80% or at least 90% of the peptides used.

Alternative embodiments include at least one peptide comprising at least five peptides of the RAS protein wherein each of the five peptides comprises a region of at least 8 amino acids including position 13 of the RAS protein. Each of the at least five peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 13 with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 13 to one of SEQ ID NOs: 1-6, 13, 20, 21 and 22. Each of the at least five peptides has a point mutation at the amino acid corresponding to position 13 of the RAS protein, independently selected from a G13A, G13C, G13D, G13R, G13S or a G13V mutation, and the point mutation of each peptide is different from the point mutation of the other peptides.

In another embodiment, the at least one peptide suitable for eliciting an immune response consists of six peptides of the RAS protein wherein each peptide comprises a region of at least 8 amino acids including position 12 of the RAS protein. Each of the peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 12 with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 12 to one of SEQ ID NOs: 7-12 and 14-19. Each of the peptides has a point mutation at the amino acid corresponding to position 12 of the RAS protein, which is selected from a G12A, G12C, G12D, G12R, G12S or a G12V mutation, and the point mutation of each peptide is different from the point mutation of the other peptides.

In a further embodiment, the at least one peptide suitable for eliciting an immune response consists of a first, second, third and fourth peptide of the RAS protein wherein each of the first, second and third peptides comprises a region of at least 8 amino acids including position 12 of the RAS protein, and the fourth peptide of the RAS protein comprises a region of at least 8 amino acids including position 13 of the RAS protein. Each of the first, second, third and fourth peptides independently has at least 20%, at least 25%, at least 30%, at least 40%, at least 50%, at least 60%, at least 66%, at least 75%, at least 85%, at least 95%, at least 99% or 100% sequence identity at positions other than the region including position 12 or 13 respectively with the RAS protein, and/or independently has at least 20%, at least 25%, at least 30%, at least 40%, at least 50%, at least 60%, at least 66%, at least 75%, at least 85%, at least 95%, at least 99% or 100% sequence identity at positions other than the region including position 12 or 13 respectively to one of SEQ ID NOs: 7-12, 14-19, 1-6, 13, 20, 21 and 22 respectively. Each of the first, second, third and fourth peptides has a point mutation at the amino acid corresponding to said position 12 or 13 of the RAS protein, respectively. In some embodiments, the first peptide is a peptide having a G12A mutation, the second peptide is a peptide having a G12R mutation, the third peptide is a peptide having a G12S mutation, and the fourth peptide is a peptide having a G13C mutation.

The at least one peptide used according to the present invention is a peptide which corresponds the RAS protein fragments displayed by MHC II molecules on the surface of cells. Thus, the at least one peptide used according to the present invention is a peptide which corresponds to the protein fragments which result from the intracellular proteolytic degradation of RAS proteins, which can then be displayed on HLA molecules, and to which individuals generally have a reactive T cell in their T cell repertoire.

In a further aspect of the present invention, there is provided at least one T-cell, or a T-cell preparation comprising T-cells, specific for the at least one peptide as described above, when presented on an MHC molecule, for use in the treatment of cancer by simultaneous or sequential administration with an anti-metabolite chemotherapeutic agent. The at least one T-cell may be produced by stimulating at least one reactive T-cell with at least one peptide of the RAS protein. For example, in one embodiment, the at least one T-cell comprises a plurality of T-cells wherein a first and a second T-cell are specific for a first and a second peptide, respectively, corresponding to a fragment of the RAS protein, wherein each peptide comprises a region of at least 8 amino acids including position 13 of the RAS protein, wherein each of the first and second T-cells is specific for a point mutation at the amino acid of the peptide corresponding to said position 13 and the point mutation for which the first T-cell is specific is different from the point mutation for which the second T-cell is specific. In another embodiment, for example, the at least one T-cell comprises a plurality of T-cells specific for a peptide corresponding to a fragment of the RAS protein, wherein the peptide comprises a region of at least 8 amino acids including position 13 of the RAS protein, wherein each T-cell is specific for a point mutation at the amino acid of the peptide corresponding to said position 13.

The at least one peptide, at least one T-cell and T-cell preparations described above are for use in the treatment of cancer and are administered simultaneously or sequentially with an anti-metabolite chemotherapeutic agent. In some embodiments the anti-metabolite chemotherapeutic agent is a pyrimidine analogue, or a pharmaceutically acceptable salt thereof. In preferred embodiments, the anti-metabolite chemotherapeutic agent is gemcitabine or a pharmaceutically acceptable salt thereof. In some embodiments, a pharmaceutically acceptable salt of gemcitabine is gemcitabine hydrochloride.

The at least one peptide, at least one T-cell or T-cell preparation for use according to the present invention is used for the treatment of cancer. In some embodiments, the cancer is cancer that arises due to mutation in the RAS protein, in particular a mutation that corresponds to the point mutation in the peptide or peptides that is adminstered. In some embodiments, the cancer is one or more of non-small cell lung cancer, pancreatic cancer, bladder cancer, ovarian cancer and breast cancer. In preferred embodiments, the cancer is pancreatic cancer. In more preferred embodiments, the cancer is resected pancreatic cancer. In some embodiments, the at least one peptide comprises a peptide having a G13C point mutation, the at least one T-cell is specific for a peptide having a G13C mutation or the T-cell preparation comprises T-cells specific for a peptide having a G13C mutation, and is for use in the treatment of cancer by simultaneous or sequential administration with an anti-metabolite chemotherapeutic agent. In such embodiments, it is preferred that the cancer is pancreatic cancer. In another embodiment, the at least one peptide comprises a peptide having a G13D mutation, the at least one T-cell is specific for a peptide having a G13D mutation or the T-cell preparation comprises T-cells specific for a peptide having a G13D mutation, and is for use in the treatment of cancer by simultaneous or sequential administration with an anti-metabolite chemotherapeutic agent. In particular, it has been found that the treatment of cancer by simultaneous or sequential administration of at least one peptide significantly improves the immune response to the at least one peptide after the following dosage regimen as compared to the administration of a peptide vaccine alone: week 1: peptide only; week 2—peptide only; week 3—peptide only; week 4—peptide and anti-metabolite chemotherapeutic agent; week 5—anti-metabolite chemotherapeutic agent only; week 6—peptide and anti-metabolite chemotherapeutic agent; week 7—no treatment; and week 8—peptide and anti-metabolite chemotherapeutic agent.

Pharmaceutical compositions comprising the at least one peptide, at least one T-cell or T-cell preparation described above are also provided for use according to the present invention. Such pharmaceutical compositions may also comprise at least one pharmaceutically acceptable carrier, diluent and/or excipient. In some embodiments, the pharmaceutical composition further comprises one or more additional active ingredients and/or adjuvants. In certain embodiments the pharmaceutical composition may further comprise one or more ingredients therapeutically effective for the same disease indication. In some embodiments, the pharmaceutical composition also comprises granulocyte macrophage colony-stimulating factor (GM-CSF).

In some embodiments, the anti-metabolite chemotherapeutic agent is administered simultaneously with the at least one peptide, at least one T-cell, T-cell preparation or pharmaceutical composition. Thus, in such embodiments, the anti-metabolite chemotherapeutic agent is administered at the same time as the at least one peptide, at least one T-cell, T-cell preparation or pharmaceutical composition.

In other embodiments, the anti-metabolite chemotherapeutic agent is administered sequentially with the at least one peptide, at least one T-cell, T-cell preparation or pharmaceutical composition. In some embodiments, the at least one peptide at least one T-cell, T-cell preparation or pharmaceutical composition is administered, and is followed by the administration of the anti-metabolite chemotherapeutic agent. In some embodiments, at each instance of sequential administration the anti-metabolite chemotherapeutic agent is administered within 6 hours of the at least one peptide at least one T-cell, T-cell preparation or pharmaceutical composition. In other embodiments, at each instance of sequential administration the anti-metabolite chemotherapeutic agent is administered within 12 hours of the at least one peptide at least one T-cell, T-cell preparation or pharmaceutical composition. In further embodiments, at each instance of sequential administration the anti-metabolite chemotherapeutic agent is administered within 18 hours of the at least one peptide, at least one T-cell, T-cell preparation or pharmaceutical composition. In yet further embodiments, at each instance of sequential administration the anti-metabolite chemotherapeutic agent is administered within 24 hours of the at least one peptide, at least one T-cell, T-cell preparation or pharmaceutical composition. In preferred embodiments, at each instance of sequential administration the anti-metabolite chemotherapeutic agent is administered in the 24 hours immediately following the administration of the at least one peptide, at least one T-cell, T-cell preparation or pharmaceutical composition.

In some embodiments, the at least one peptide, at least one T-cell, T-cell preparation or pharmaceutical composition and the anti-metabolite chemotherapeutic agent are administered simultaneously or sequentially more than once to the same patient. In some embodiments, the at least one peptide and the anti-metabolite chemotherapeutic agent are administered at least twice (i.e. at at least two instances). In other embodiments, the at least one peptide and the anti-metabolite chemotherapeutic agent are administered at least three times (i.e. at at least three instances). In further embodiments, the at least one peptide, at least one T-cell, T-cell preparation or pharmaceutical composition and the anti-metabolite chemotherapeutic agent are administered more than three times (i.e. at more than three instances). In some embodiments, at each instance of administration of the at least one peptide, at least one T-cell, T-cell preparation or pharmaceutical composition and the anti-metabolite chemotherapeutic agent is separated by at least one week. In other embodiments, each instance of administration of the at least one peptide, at least one T-cell, T-cell preparation or pharmaceutical composition and the anti-metabolite chemotherapeutic agent is separated by at least two weeks. In some embodiments, each instance of administration is separated by more than two weeks.

In some embodiments, the anti-metabolite chemotherapeutic agent is administered alone, one or more times, before or after simultaneous or sequential administration with the at least one peptide, at least one T-cell, T-cell preparation or pharmaceutical composition of the invention. In other embodiments, the at least one peptide, at least one T-cell, T-cell preparation or pharmaceutical composition is administered alone, one or more times, before or after simultaneous or sequential administration with the anti-metabolite chemotherapeutic agent.

Thus in some embodiments, the first administration of the anti-metabolite chemotherapeutic agent is delayed with respect to the first administration of the at least one peptide, at least one T-cell, T-cell preparation or pharmaceutical composition. In some embodiments, the first administration of the anti-metabolite chemotherapeutic agent is at least one week after the first administration of the at least one peptide, at least one T-cell, T-cell preparation or pharmaceutical composition. In other embodiments, the first administration of the anti-metabolite chemotherapeutic agent is at least two weeks after the first administration of the at least one peptide, at least one T-cell, T-cell preparation or pharmaceutical composition. In further embodiments, the first administration of the anti-metabolite chemotherapeutic agent is at least three weeks after the first administration of the at least one peptide, at least one T-cell, T-cell preparation or pharmaceutical composition. In particularly preferred embodiments, regardless of the delay between the first administration of each of the at least one peptide, at least one T-cell, T-cell preparation or pharmaceutical composition and the anti-metabolite chemotherapeutic agent, the anti-metabolite chemotherapeutic agent is administered within 24 hours of the administration of the at least one peptide, at least one T-cell, T-cell preparation or pharmaceutical composition. In particular, a delay of three weeks between the first administration of the at least one peptide, at least one T-cell, T-cell preparation or pharmaceutical composition and the first administration of the anti-metabolite chemotherapeutic agent has been found to have significant effects on the immune response recorded.

In some embodiments wherein the cancer is resected pancreatic cancer, the first administration of the anti-metabolite chemotherapeutic agent is 12 weeks or fewer after the surgical resection of pancreatic cancer. In some embodiments, the first administration is 10 weeks or fewer after surgical resection of pancreatic cancer. In other embodiments, the first administration of the anti-metabolite chemotherapeutic agent is 8 weeks or fewer after surgical resection of pancreatic cancer.

The at least one peptide, at least one T-cell, T-cell preparation or pharmaceutical composition for use according to the present invention may be administered to a subject by any suitable delivery technique known to those skilled in the art. For example, among other techniques, the at least one peptide, at least one T-cell, T-cell preparation or pharmaceutical composition may be administered to a subject by injection, in the form of a solution, in the form of liposomes or in dry form (for example, in the form of coated particles, etc). In some embodiments, the at least one peptide or pharmaceutical composition is administered in an amount of between 0.01 mg and 10 mg of the at least one peptide, per dose. In other embodiments, the at least one peptide or the pharmaceutical composition is administered in an amount of between 0.1 mg and 2 mg of the at least one peptide, per dose. In some embodiments, the at least one peptide or the pharmaceutical composition is administered in an amount of 0.1 mg of the at least one peptide, per dose. In another embodiment, the at least one peptide or the pharmaceutical composition is administered in an amount of 0.7 mg of the at least one peptide, per dose. The dosage depends on the number of different peptides administered to the patient. For example, when the at least one peptide consists of only one type of point mutation, the at least one peptide or the pharmaceutical composition is preferably administered in an amount of 0.1 mg of the at least one peptide, per dose. In another example, when the at least one peptide comprises seven or more types of point mutation, the at least one peptide or pharmaceutical composition is preferably administered in an amount of 0.7 mg of the at least one peptide, per dose.

In some embodiments, the at least one T-cell or T-cell preparation is administered by intra-venous injection and/or infusion, and is administered in an amount, for example, of between $10^6$ and $10^{12}$ of each T-cell specific for a peptide of the invention.

The anti-metabolite chemotherapeutic agent may be administered to a subject by any delivery technique known to those skilled in the art. For example, in some embodiments, the anti-metabolite chemotherapy agent is administered by cannula, central line or by peripherally inserted central catheter. In some embodiments, the anti-metabolite chemotherapeutic agent is administered in an amount of between 100 and 10,000 $mg/m^2$ of body surface area. In some embodiments, the anti-metabolite chemotherapeutic agent is administered in an amount of between 500 and 2000 $mg/m^2$ of body surface area. In other embodiments, the anti-metabolite chemotherapeutic agent is administered in an amount of 1000 $mg/m^2$ of body surface area.

In further embodiments of the present invention, there is provided a kit comprising a first product comprising at least one peptide, T cell or pharmaceutical composition, as described above and a second product comprising a supply of an anti-metabolite chemotherapeutic agent as described above. The first and second products are provided in separate vials or compartments. In some embodiments, the kit further comprises instructions for administration of the first and second products.

Tables

TABLE 1

Position 13 mutated RAS peptides of
SEQ ID NOs: 1-6

1          13              30
MTEYKLVVVGAGCVGKSALTIQLIQNHFVD

MTEYKLVVVGAGRVGKSALTIQLIQNHFVD

MTEYKLVVVGAGDVGKSALTIQLIQNHFVD

TABLE 1-continued

Position 13 mutated RAS peptides of
SEQ ID NOs: 1-6

MTEYKLVVVGAGVVGKSALTIQLIQNHFVD

MTEYKLVVVGAGAVGKSALTIQLIQNHFVD

MTEYKLVVVGAGSVGKSALTIQLIQNHFVD

TABLE 2

Position 12 mutated RAS peptides of
SEQ ID NOs: 7-12

```
       1           12                  30
MTEYKLVVVGAAGVGKSALTIQLIQNHFVD

MTEYKLVVVGACGVGKSALTIQLIQNHFVD

MTEYKLVVVGADGVGKSALTIQLIQNHFVD

MTEYKLVVVGARGVGKSALTIQLIQNHFVD

MTEYKLVVVGASGVGKSALTIQLIQNHFVD

MTEYKLVVVGAVGVGKSALTIQLIQNHFVD
```

TABLE 3

Peptides contained in TG01 of
SEQ ID NOs: 13-19

```
  5                  21
KLVVVGAGDVGKSALTI

KLVVVGAAGVGKSALTI

KLVVVGACGVGKSALTI

KLVVVGADGVGKSALTI

KLVVVGARGVGKSALTI

KLVVVGASGVGKSALTI

KLVVVGAVGVGKSALTI
```

TABLE 4

Peptides contained in TG02 of
SEQ ID NOs: 13-20

```
  5                  21
KLVVVGAGCVGKSALTI

KLVVVGAGDVGKSALTI

KLVVVGAAGVGKSALTI

KLVVVGACGVGKSALTI

KLVVVGADGVGKSALTI

KLVVVGARGVGKSALTI

KLVVVGASGVGKSALTI

KLVVVGAVGVGKSALTI
```

EXAMPLES

Example 1

A phase I/II trial was carried out to investigate the safety and immunological response of adjuvant treatment of resected pancreatic cancer with RAS peptide vaccination (TG01) alone and then combined with gemcitabine adjuvant chemotherapy.

Patients received TG01 together with an immune modulator, GM-CSF, within 1-8 weeks after surgery. Between 3-7 weeks after TG01/GM-CSF treatment started, patients also received gemcitabine. The patients were assessed for safety and immune responses by week 11 after receiving at least one cycle of gemcitabine.

Initially, six patients were treated with TG01 and GM-CSF and, at week 11, the safety and immune responses were used to assess how the study would continue, as set out below.

If, at week 11:
  0 out of 6 patients showed an immune response, and/or 3 out of 6 patients showed a dose limiting toxicity (DLT), the study would be terminated,
  1-3 out of 6 patients showed an immune response and/or 3 out of 6 patients showed a DLT, then a further 6 patients would be enrolled in the study,
  4 or more out of 6 patients showed an immune response and/or 2 or fewer out of 6 patients showed a DLT, then the phase II study would be initiated.

It was decided that, if the phase I enrolment was expanded to 12 patients, then at week 11, if:
  fewer than 4 out of 12 patients showed an immune response and/or more than 4 out of 12 patients showed a DLT, then the study would be terminated,
  4 or more out of 12 patients showed an immune response and/or 4 or fewer out of 12 patients showed a DLT, a phase II study would be initiated.

Thus, a phase II study would be initiated if:
  a) 4 or more out of 6 patients showed an immune response and 2 or fewer out of 6 patients showed a DLT at week 11, or
  b) 4 or more out of 12 patients showed an immune response and 4 or fewer out of 12 patients showed a DLT at week 11.

Preparation of Trial Treatment

TG01 was provided in 2R glass vials containing 2.1 mg of TG01 and the content of one vial of TG01 was dissolved in 0.3 mL of sterile water for injection (7 mg/mL). The solution was used within 6 hours after reconstitution.

GM-CSF was provided in vials containing 0.1 mg and the content of one vial was dissolved in 0.33 mL of sterile water for injection (0.30 mg/mL). The solution was used within 6 hours after reconstitution.

Gemcitabine was administered at a dose of 1000 mg/m$^2$. The drug was provided in vials of 200 mg and 1 g for reconstitution in saline to be given via intravenous injection.

For DTH, the content of one vial of TG01 was dissolved in 0.3 mL sterile water for injection. The solution was used within 6 hours after reconstitution.

TG01 and GM-CSF Dose and Administration

TG01 and GM-CSF was given on days 1, 3, 5, 8, 15, 22 and every 2 weeks until the end of chemotherapy (with day 1 defined as the first day of TG01 treatment which was 1-8 weeks after surgery). After the end of chemotherapy, in patients who had not shown recurrence and/or who had a positive immune response during the study treatment period, further booster injections were given every 4 weeks until week 52 and then every 12 weeks for up to 2 years or until withdrawal of consent or toxicity, whichever was the earliest.

The TG01 dose was 0.70 mg (0.10 mL injection of a TG01 solution at 7 mg/mL reconstituted in water for injection). The GM-CSF dose was 0.03 mg (~0.10 mL injection of a GM-CSF solution at 0.3 mg/mL reconstituted in water for injection).

Both study drugs were administered by intradermal injections into the back of the upper arm with GM-CSF being administered 10-15 minutes before the injection of TG01.

Chemotherapy Dosage and Administration

Patients received gemcitabine starting at least 3 weeks after initiation of TG01 and GM-CSF (Day 22, 36 or 50 of the initial treatment period) but not later than 12 weeks from the date of surgery. The day of the first dose of TG01 and GM-CSF was considered as Day 1 of the chemotherapy treatment period. Gemcitabine was given as 1000 mg/m$^2$, intravenously, over 30 minutes on days 1, 8 and 15 of a four week cycle for six cycles in total.

DTH Dosage and Administration

TG01 was given on days 1, 8, 15, 22, 36, 50, and 64 in the lower area of the contralateral arm.

The DTH-test dose was prepared on the day of treatment, and was 0.10 mL of TG01 at 7 mg/mL water for injection solution, prepared for intradermal injection in a sterile syringe.

Chemotherapy Dosing Criteria

Gemcitabine:

Before the administration of gemcitabine, at the start of each new treatment cycle, patients were assessed to ensure that they satisfied the gemcitabine prescribing information from the product manufacturers.

Results and Discussion

The study was expanded from 6 to 9 patients, and the results obtained therefrom are discussed below.

TG01-specific immune responses were found in all 9 subjects by week 11, and no DLTs were reported.

The safety profile was as expected for patients post pancreatic surgery who received chemotherapy. There was one adverse event considered related to TG01/GM-CSF alone, which was an injection site reaction. One patient experienced three events that were related to TG01/GM-CSF and gemcitabine (nausea, vomiting and flu-like symptoms). Adverse events related to gemcitabine were as expected with grade 3/4 neutropenia being the principal related adverse event. Interruptions or reductions in dose of gemcitabine were required in these cases.

Four serious adverse events were reported in two patients. One patient experienced pulmonary infection and two episodes of fever, all considered related to gemcitabine. One patient experienced nausea also considered unrelated to treatment with TG01 and gemcitabine.

From no DTH reaction at baseline (week 1), four patients (44%) developed a DTH reaction prior to initiation of gemcitabine at the end of week 3 (FIGS. 1 and 2). This increased to seven patients (77%) with positive DTH after the first cycle of gemcitabine (week 6), and to all nine patients (100%) after the first dose of gemcitabine in the second cycle (week 8) (FIGS. 1 and 2). This demonstrates that a Th1 polarised response to TG01 was induced in all patients after concomitant treatment with TG01 and gemcitabine at week 8.

It was also found that there was no reduction or abrogation of established immune responses, such that the induced immune responses were persistent (FIG. 2). Indeed, the number of patients showing an immune response following administration of both TG01 and gemcitabine in the second cycle (week 8) was significantly greater than when TG01 was administered alone (FIG. 2).

These results demonstrate the unexpected finding that the combination of TG01 and gemcitabine is effective in inducing an immune response in cancer patients, and that the induced response immune response is robust. In particular, the algorithm for continuing the study to phase II (i.e. at week 11, if 4 or more out of 6 patients showed an immune response and/or 2 or fewer out of 6 patients showed a DLT, then the phase II study would be initiated) demonstrates that the expectation was that perhaps 50% of patients would display an immune response at week 11. That all patients were shown to have an immune response at week 11 was therefore very surprising to the study designers.

The invention claimed is:

1. A method of treating cancer in humans, wherein the cancer comprises a cell which expresses a mutated RAS protein having a point mutation at position 12 or 13 of a wild-type RAS protein, the method comprising the step of simultaneously or sequentially administering at least one peptide and an anti-metabolite chemotherapeutic agent to a human patient in need thereof, wherein the at least one peptide is suitable for eliciting an immune response, the or each peptide corresponds to a fragment of a reference wild-type RAS protein but has one point mutation thereof, the or each peptide comprises a region of at least 8 amino acids which includes position 12 or 13 of the reference wild-type RAS protein, and wherein the position of the point mutation of the or each peptide corresponds to the position of the point mutation of the mutated RAS protein expressed by the cell, and wherein the point mutation is selected from a G13A, G13C, G13D, G13R, G13S, G13V, G12A, G12C, G12D, G12R, G12S or a G12V mutation.

2. A method according to claim 1, wherein the at least one peptide comprises two or more peptides, each peptide having a different point mutation.

3. A method according to claim 1, wherein the at least one peptide comprises:
 a peptide having a G13D mutation
 a peptide having a G12A mutation
 a peptide having a G12C mutation
 a peptide having a G12D mutation
 a peptide having a G12R mutation
 a peptide having a G12S mutation, and
 a peptide having a G12V mutation.

4. A method according to claim 3, wherein the at least one peptide comprises a peptide consisting of the sequence represented by SEQ ID NO: 13, a peptide consisting of the sequence represented by SEQ ID NO: 14, a peptide consisting of the sequence represented by SEQ ID NO: 15, a peptide consisting of the sequence represented by SEQ ID NO: 16, a peptide consisting of the sequence represented by SEQ ID NO: 17, a peptide consisting of the sequence represented by SEQ II) NO: 18 and a peptide consisting of the sequence represented by SEQ ID NO: 19.

5. A method according to claim 1, wherein the at least one peptide comprises:
 a peptide having a G13D mutation
 a peptide having a G13C mutation
 a peptide having a G12A mutation
 a peptide having a G12C mutation
 a peptide having a G12D mutation
 a peptide having a G12R mutation
 a peptide having a G12S mutation, and
 a peptide having a G12V mutation.

6. A method according to claim 5, wherein the at least one peptide comprises a peptide consisting of the sequence represented by SEQ ID NO: 13, a peptide consisting of the sequence represented by SEQ. ID NO: 14, a peptide consisting of the sequence represented by SEQ ID NO: 15, a peptide consisting of the sequence represented by SEQ ID NO: 16, a peptide consisting of the sequence represented by SEQ ID NO: 17, a peptide consisting of the sequence represented by SEQ ID NO: 18, a peptide consisting of the sequence represented by SEQ ID NO: 19 and a peptide consisting of the sequence represented by SEQ ID NO: 20.

7. A method according to claim 1, wherein the anti-metabolite chemotherapeutic agent is a pyrimidine analogue or a pharmaceutically acceptable salt thereof.

8. A method according to claim 7, wherein the pyrimidine analogue is gemcitabine or a pharmaceutically acceptable salt thereof.

9. A method according to claim 1, wherein the at least one peptide comprises a peptide consisting of the sequence represented by SEQ ID NO: 13, a peptide consisting of the sequence represented by SEQ ID NO: 14, a peptide consisting of the sequence represented by SEQ ID NO: 15, a peptide consisting of the sequence represented by SEQ ID NO: 16, a peptide consisting of the sequence represented by SEQ ID NO: 17, a peptide consisting of the sequence represented by SEQ ID NO: 18, a peptide consisting of the sequence represented by SEQ ID NO: 19 and a peptide consisting of the sequence represented by SEQ ID NO: 20, and wherein the anti-metabolite chemotherapeutic agent is gemcitabine.

10. A method according to claim 1, wherein the cancer is selected from the group consisting of: pancreatic cancer and resected pancreatic cancer.

11. A method according to claim 1, wherein the method comprises the step of first administering the anti-metabolite chemotherapeutic agent at least three weeks after the first dose of the at least one peptide.

12. A method according to claim 10, wherein the cancer is resected pancreatic cancer and the method comprises the step of first administering the anti-metabolite chemotherapeutic agent 12 weeks or fewer after surgical resection of the pancreatic cancer.

13. A method according to claim 1, wherein the method comprises the step of administering the anti-metabolite chemotherapeutic agent within 24 hours of the at least one peptide.

14. A method according to claim 13, wherein the method comprises the step of administering the anti-metabolite chemotherapeutic agent after the at least one peptide has been administered.

15. A method according to claim 1, wherein the method comprises the step of administering the at least one peptide at a dosage selected from the group consisting of: 0.01-10 mg per dose, 0.1-2 mg per dose and 0.7 mg per dose.

16. A method according to claim 1, wherein the method comprises the step of administering the anti-metabolite chemotherapeutic agent at a dosage selected from the group consisting of: 100-10,000 mg/m$^2$, 500-2000 mg/m$^2$ and 1000 mg/m$^2$.

17. A method according to claim 1, wherein the method comprises the step of administering the at least one peptide and the anti-metabolite chemotherapeutic agent simultaneously or sequentially at at least two instances.

18. A method of treating cancer in humans, wherein the cancer comprises a cell which expresses a mutated RAS protein having a point mutation at position 12 or 13 of a wild-type RAS protein, wherein the method comprises the step of simultaneously or sequentially administering, to a human patient in need thereof, an anti-metabolite chemotherapeutic agent and a pharmaceutical composition, wherein the pharmaceutical composition comprises at least one peptide, wherein the at least one peptide is suitable for eliciting an immune response, the or each peptide corresponds to a fragment of a reference wild-type RAS protein but has one point mutation thereof, the or each peptide comprises a region of at least 8 amino acids which includes position 12 or 13 of the reference wild-type RAS protein, and wherein the position of the point mutation of the or each peptide corresponds to the position of the point mutation of the mutated RAS protein expressed by the cell, and wherein the point mutation is selected from a G13A, G13C, G13D, G13R, G13S, G13V, G12A, G12C, G12D, G12R, G12S or a G12V mutation.

* * * * *

SEQUENCE LISTING

```
<160> NUMBER OF SEQ ID NOS: 23

<210> SEQ ID NO 1
<211> LENGTH: 30
<212> TYPE: PRT
<213> ORGANISM: Homo sapiens

<400> SEQUENCE: 1

Met Thr Glu Tyr Lys Leu Val Val Val Gly Ala Gly Cys Val Gly Lys
1               5                   10                  15

Ser Ala Leu Thr Ile Gln Leu Ile Gln Asn His Phe Val Asp
            20                  25                  30

<210> SEQ ID NO 2
<211> LENGTH: 30
<212> TYPE: PRT
<213> ORGANISM: Homo sapiens

<400> SEQUENCE: 2

Met Thr Glu Tyr Lys Leu Val Val Val Gly Ala Gly Arg Val Gly Lys
1               5                   10                  15
```

Ser Ala Leu Thr Ile Gln Leu Ile Gln Asn His Phe Val Asp
            20                  25                  30

<210> SEQ ID NO 3
<211> LENGTH: 30
<212> TYPE: PRT
<213> ORGANISM: Homo sapiens

<400> SEQUENCE: 3

Met Thr Glu Tyr Lys Leu Val Val Val Gly Ala Gly Asp Val Gly Lys
1               5                   10                  15

Ser Ala Leu Thr Ile Gln Leu Ile Gln Asn His Phe Val Asp
            20                  25                  30

<210> SEQ ID NO 4
<211> LENGTH: 30
<212> TYPE: PRT
<213> ORGANISM: Homo sapiens

<400> SEQUENCE: 4

Met Thr Glu Tyr Lys Leu Val Val Val Gly Ala Gly Val Val Gly Lys
1               5                   10                  15

Ser Ala Leu Thr Ile Gln Leu Ile Gln Asn His Phe Val Asp
            20                  25                  30

<210> SEQ ID NO 5
<211> LENGTH: 30
<212> TYPE: PRT
<213> ORGANISM: Homo sapiens

<400> SEQUENCE: 5

Met Thr Glu Tyr Lys Leu Val Val Val Gly Ala Gly Ala Val Gly Lys
1               5                   10                  15

Ser Ala Leu Thr Ile Gln Leu Ile Gln Asn His Phe Val Asp
            20                  25                  30

<210> SEQ ID NO 6
<211> LENGTH: 30
<212> TYPE: PRT
<213> ORGANISM: Homo sapiens

<400> SEQUENCE: 6

Met Thr Glu Tyr Lys Leu Val Val Val Gly Ala Gly Ser Val Gly Lys
1               5                   10                  15

Ser Ala Leu Thr Ile Gln Leu Ile Gln Asn His Phe Val Asp
            20                  25                  30

<210> SEQ ID NO 7
<211> LENGTH: 30
<212> TYPE: PRT
<213> ORGANISM: Homo sapiens

<400> SEQUENCE: 7

Met Thr Glu Tyr Lys Leu Val Val Val Gly Ala Ala Gly Val Gly Lys
1               5                   10                  15

Ser Ala Leu Thr Ile Gln Leu Ile Gln Asn His Phe Val Asp
            20                  25                  30

<210> SEQ ID NO 8
<211> LENGTH: 30
<212> TYPE: PRT
<213> ORGANISM: Homo sapiens

```
<400> SEQUENCE: 8

Met Thr Glu Tyr Lys Leu Val Val Val Gly Ala Cys Gly Val Gly Lys
1               5                   10                  15

Ser Ala Leu Thr Ile Gln Leu Ile Gln Asn His Phe Val Asp
            20                  25                  30

<210> SEQ ID NO 9
<211> LENGTH: 30
<212> TYPE: PRT
<213> ORGANISM: Homo sapiens

<400> SEQUENCE: 9

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp
            20                  25                  30

<210> SEQ ID NO 10
<211> LENGTH: 30
<212> TYPE: PRT
<213> ORGANISM: Homo sapiens

<400> SEQUENCE: 10

Met Thr Glu Tyr Lys Leu Val Val Val Gly Ala Arg Gly Val Gly Lys
1               5                   10                  15

Ser Ala Leu Thr Ile Gln Leu Ile Gln Asn His Phe Val Asp
            20                  25                  30

<210> SEQ ID NO 11
<211> LENGTH: 30
<212> TYPE: PRT
<213> ORGANISM: Homo sapiens

<400> SEQUENCE: 11

Met Thr Glu Tyr Lys Leu Val Val Val Gly Ala Ser Gly Val Gly Lys
1               5                   10                  15

Ser Ala Leu Thr Ile Gln Leu Ile Gln Asn His Phe Val Asp
            20                  25                  30

<210> SEQ ID NO 12
<211> LENGTH: 30
<212> TYPE: PRT
<213> ORGANISM: Homo sapiens

<400> SEQUENCE: 12

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp
            20                  25                  30

<210> SEQ ID NO 13
<211> LENGTH: 17
<212> TYPE: PRT
<213> ORGANISM: Homo sapiens

<400> SEQUENCE: 13

Lys Leu Val Val Val Gly Ala Gly Asp Val Gly Lys Ser Ala Leu Thr
1               5                   10                  15

Ile

<210> SEQ ID NO 14
```

```
<211> LENGTH: 17
<212> TYPE: PRT
<213> ORGANISM: Homo sapiens

<400> SEQUENCE: 14

Lys Leu Val Val Val Gly Ala Ala Gly Val Gly Lys Ser Ala Leu Thr
1               5                   10                  15

Ile

<210> SEQ ID NO 15
<211> LENGTH: 17
<212> TYPE: PRT
<213> ORGANISM: Homo sapiens

<400> SEQUENCE: 15

Lys Leu Val Val Val Gly Ala Cys Gly Val Gly Lys Ser Ala Leu Thr
1               5                   10                  15

Ile

<210> SEQ ID NO 16
<211> LENGTH: 17
<212> TYPE: PRT
<213> ORGANISM: Homo sapiens

<400> SEQUENCE: 16

Lys Leu Val Val Val Gly Ala Asp Gly Val Gly Lys Ser Ala Leu Thr
1               5                   10                  15

Ile

<210> SEQ ID NO 17
<211> LENGTH: 17
<212> TYPE: PRT
<213> ORGANISM: Homo sapiens

<400> SEQUENCE: 17

Lys Leu Val Val Val Gly Ala Arg Gly Val Gly Lys Ser Ala Leu Thr
1               5                   10                  15

Ile

<210> SEQ ID NO 18
<211> LENGTH: 17
<212> TYPE: PRT
<213> ORGANISM: Homo sapiens

<400> SEQUENCE: 18

Lys Leu Val Val Val Gly Ala Ser Gly Val Gly Lys Ser Ala Leu Thr
1               5                   10                  15

Ile

<210> SEQ ID NO 19
<211> LENGTH: 17
<212> TYPE: PRT
<213> ORGANISM: Homo sapiens

<400> SEQUENCE: 19

Lys Leu Val Val Val Gly Ala Val Gly Val Gly Lys Ser Ala Leu Thr
1               5                   10                  15

Ile

<210> SEQ ID NO 20
<211> LENGTH: 17
```

-continued

```
<212> TYPE: PRT
<213> ORGANISM: Homo sapiens

<400> SEQUENCE: 20

Lys Leu Val Val Val Gly Ala Gly Cys Val Gly Lys Ser Ala Leu Thr
1               5                   10                  15

Ile

<210> SEQ ID NO 21
<211> LENGTH: 17
<212> TYPE: PRT
<213> ORGANISM: Homo sapiens

<400> SEQUENCE: 21

Lys Leu Val Val Val Gly Ala Gly Arg Val Gly Lys Ser Ala Leu Thr
1               5                   10                  15

Ile

<210> SEQ ID NO 22
<211> LENGTH: 17
<212> TYPE: PRT
<213> ORGANISM: Homo sapiens

<400> SEQUENCE: 22

Lys Leu Val Val Val Gly Ala Gly Val Val Gly Lys Ser Ala Leu Thr
1               5                   10                  15

Ile

<210> SEQ ID NO 23
<211> LENGTH: 189
<212> TYPE: PRT
<213> ORGANISM: Homo sapiens

<400> SEQUENCE: 23

Met Thr Glu Tyr Lys Leu Val Val Val Gly Ala Gly Val Gly Lys
1               5                   10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
        50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160
```

```
Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```